(12) United States Patent
Prince et al.

(10) Patent No.: US 7,205,114 B2
(45) Date of Patent: Apr. 17, 2007

(54) OXIDIZED FUNGAL ANTIGENS AND METHODS OF MAKING AND USING THEREOF

(75) Inventors: Harry Prince, Los Angeles, CA (US); Xin Su, Irvine, CA (US); Lilly Kong, Covina, CA (US); Ken Devor, deceased, late of Garden Grove, CA (US); by Celine Ngo, legal representative, Garden Grove, CA (US); Sergei Arakelov, Santa Monica, CA (US); Wayne Hogrefe, Lake Forest, CA (US)

(73) Assignee: Focus Technologies, Inc., Cypress, CA (US)

( * ) Notice: Subject to any disclaimer, the term of this patent is extended or adjusted under 35 U.S.C. 154(b) by 138 days.

(21) Appl. No.: 10/846,380

(22) Filed: May 13, 2004

(65) Prior Publication Data

US 2005/0112708 A1 May 26, 2005

Related U.S. Application Data

(63) Continuation-in-part of application No. 10/028,181, filed on Dec. 21, 2001, now Pat. No. 6,867,004.

(51) Int. Cl.
*G01N 33/53* (2006.01)

(52) U.S. Cl. ....................................... 435/7.1

(58) Field of Classification Search ................. 435/7.1
See application file for complete search history.

(56) References Cited

U.S. PATENT DOCUMENTS

| 5,302,509 | A | 4/1994 | Cheeseman |
| 5,703,055 | A | 12/1997 | Felgner et al. |
| 6,867,004 | B2 * | 3/2005 | Prince et al. ................ 435/7.1 |
| 6,953,666 | B1 * | 10/2005 | Kinkade et al. ............. 435/7.1 |

OTHER PUBLICATIONS

Bosin and Kasper, Toxicol. (1992) 7(3):139-145.
Brock and Madigan, Biology of Microorganisms, 6th ed., Prentice Hall, Englewood Cliffs, New Jersey (1991) pp. 817-818.
Bullock, Principles and Practice of Infectious Diseases, GL Mandell et al. (eds.), Churchill Livingston, New York (1995) pp. 2340-2353 and 2365-2375.
Casadevall, Infec. and Imm. (1995) 63(11):4211-4218.
Fatiadi, Synthesis (1974) 229.
Fisher et al., Mycroses. (1997) 40:83-90.
Focus Technologies, Histoplasma Capsulatum IgG Assay Tech Sheet (2001).
Galgiani, Ann. Intern. Med. (1999) 130:293-300.
Im et al., J. Biol. Chem. (1985) 260(8):4591-4597.
Kaufman et al., J. Clin. Microbiol. (1995) 33(3):618-619.
Marzulli et al., Boll Soc. Ital. Biol. Sper. (1985) 61(1):121-127.
Pan and Jordan, Biochemistry (1998) 37(5):1357-1364.
Pizzini et al., Clin. Diagn. Lab. Immunol. (1999) 6(1):20-23.
Saha et al., Int. J. Rad. Appl. Instrum. (1989) 16(4):431-433.
Santini et al., Free Radic. Biol. Med. (1996) 20(7):915-924.
Siebert, Fortschr. Chem. Forsch. (1967) 8:470.
Sinn et al., Anal. Biochem. (1988) 170(1):186-192.
Stevens, New England J. Med. (1995) 332:1077-1082.
Tarin et al., Mol. Hum. Reprod. (1996) 2(12):895-901.
Wenzel and Pfaller, Infect. Control Hosp. Epidemiol (1991) 12:523-524.
Willard, Inorg. Syn. (1939) 1:172.
Wozniak et al., Bioorg. Med. Chem. Lett. (1998) 8(19):2641-2646.
Yang et al., Clin. Diagn. Immunol. (1997) 4:19-22.
Zancope-Oliveria et al., Clin. Diagn. Lab. Immunol. (1994) 1(4):390-393.
Zancope-Oliveria et al., Clin. Diagn. Lab. Immunol. (1994) 1(5):563-568.
Zartarian et al., Am. J. Clin. Pathol. (1997) 207:148-153.
Zierdt, J. of Parasitology (1995) 81(1):127-129.

* cited by examiner

*Primary Examiner*—Mark Navarro
(74) *Attorney, Agent, or Firm*—Foley & Lardner LLP

(57) ABSTRACT

The present invention relates to oxidized fungal antigens and methods of making and using thereof. More particularly, the present invention provides a method for producing an oxidized fungal antigen in culture filtrate. The present invention also provides for the produced oxidized fungal antigens. Devices comprising such oxidized fungal antigens, methods for testing for fungal antibodies using the oxidized fungal antigens and methods for producing anti-fungal antibodies using oxidized fungal antigens are further provided. Antigen detection devices comprising anti-fungal antibodies raised against oxidized fungal antigens produced by the present methods are further provided.

9 Claims, 4 Drawing Sheets

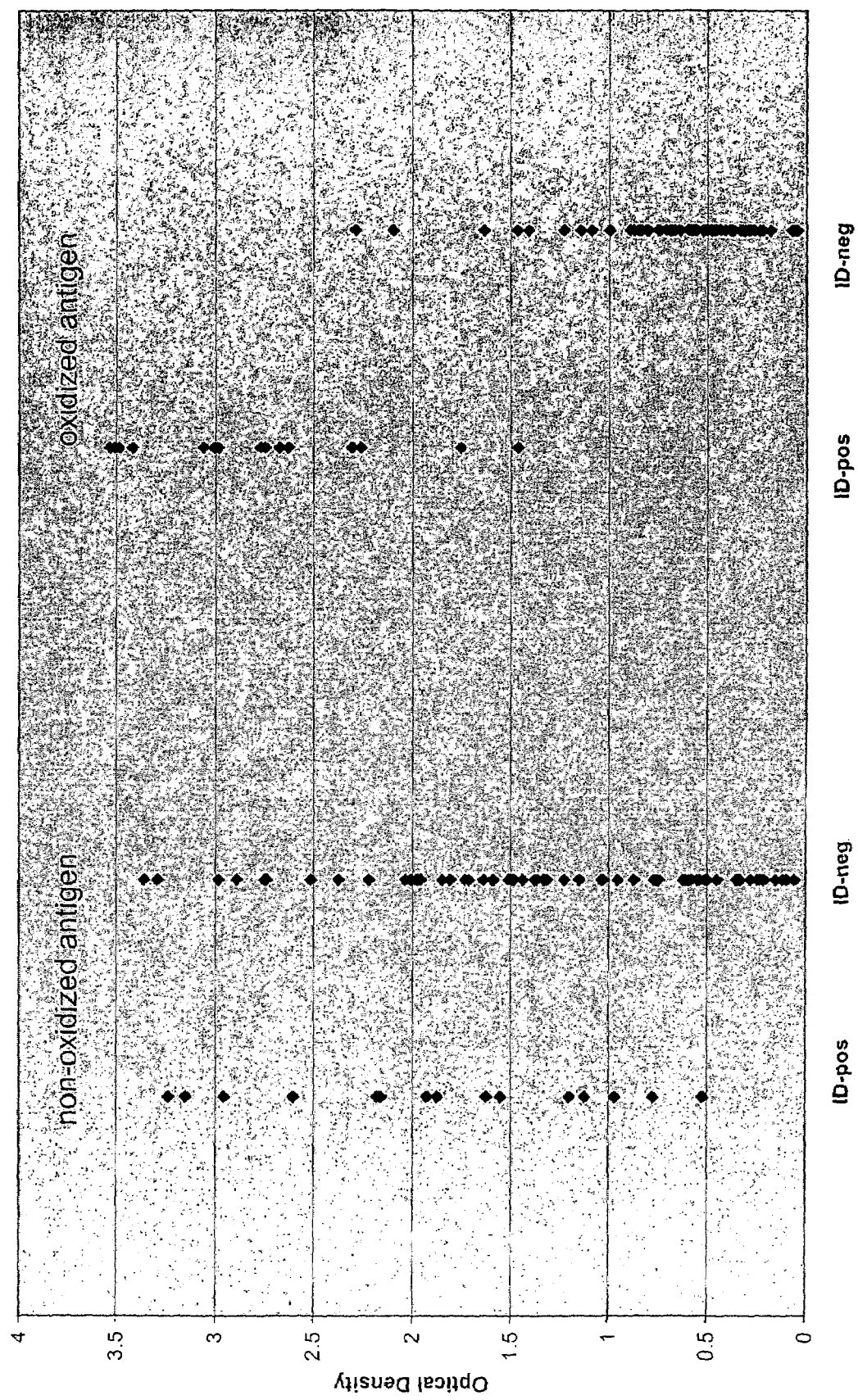
Figure 1. Histoplasma IgG ELISA

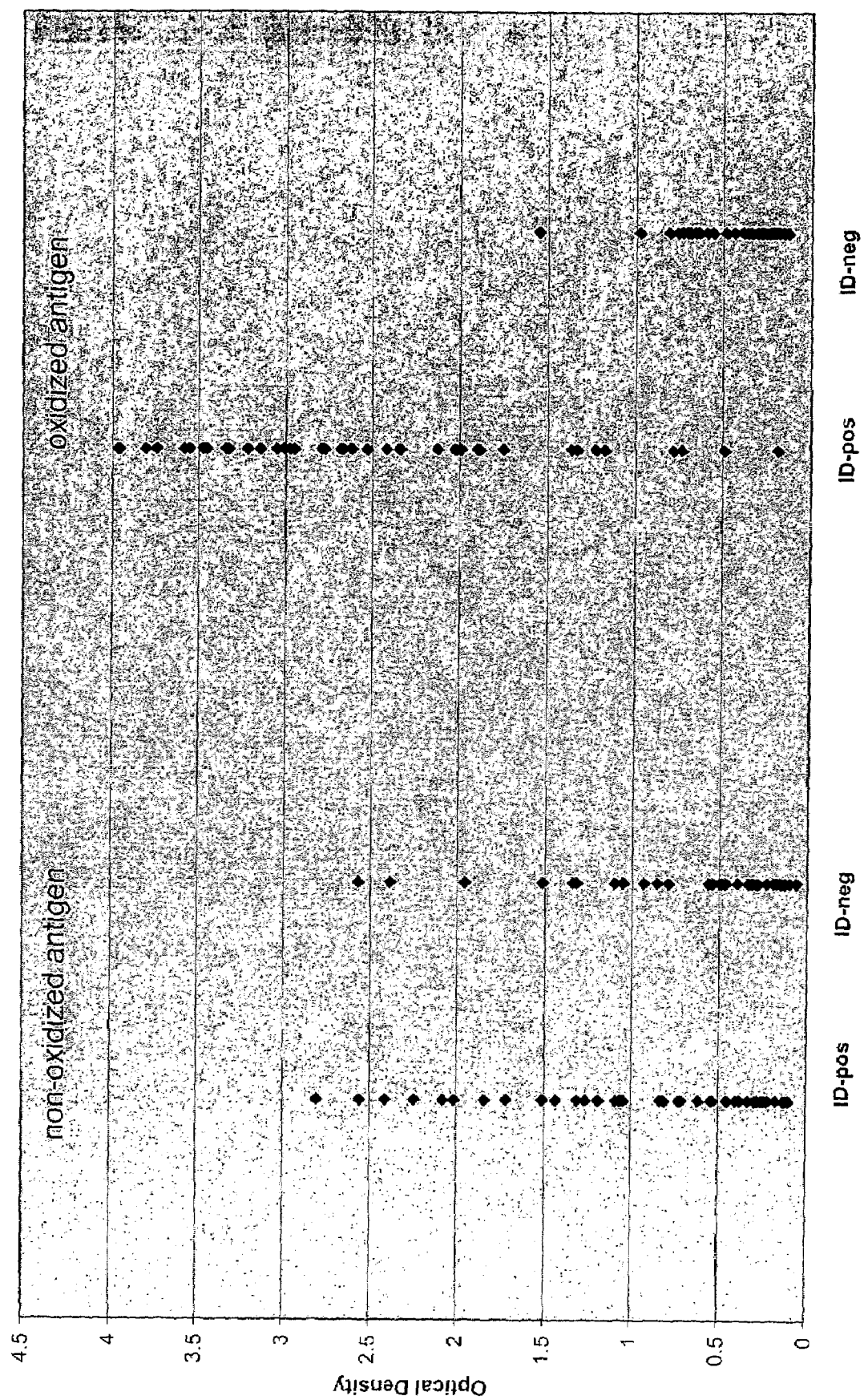
Figure 2. Coccidioides IgG ELISA

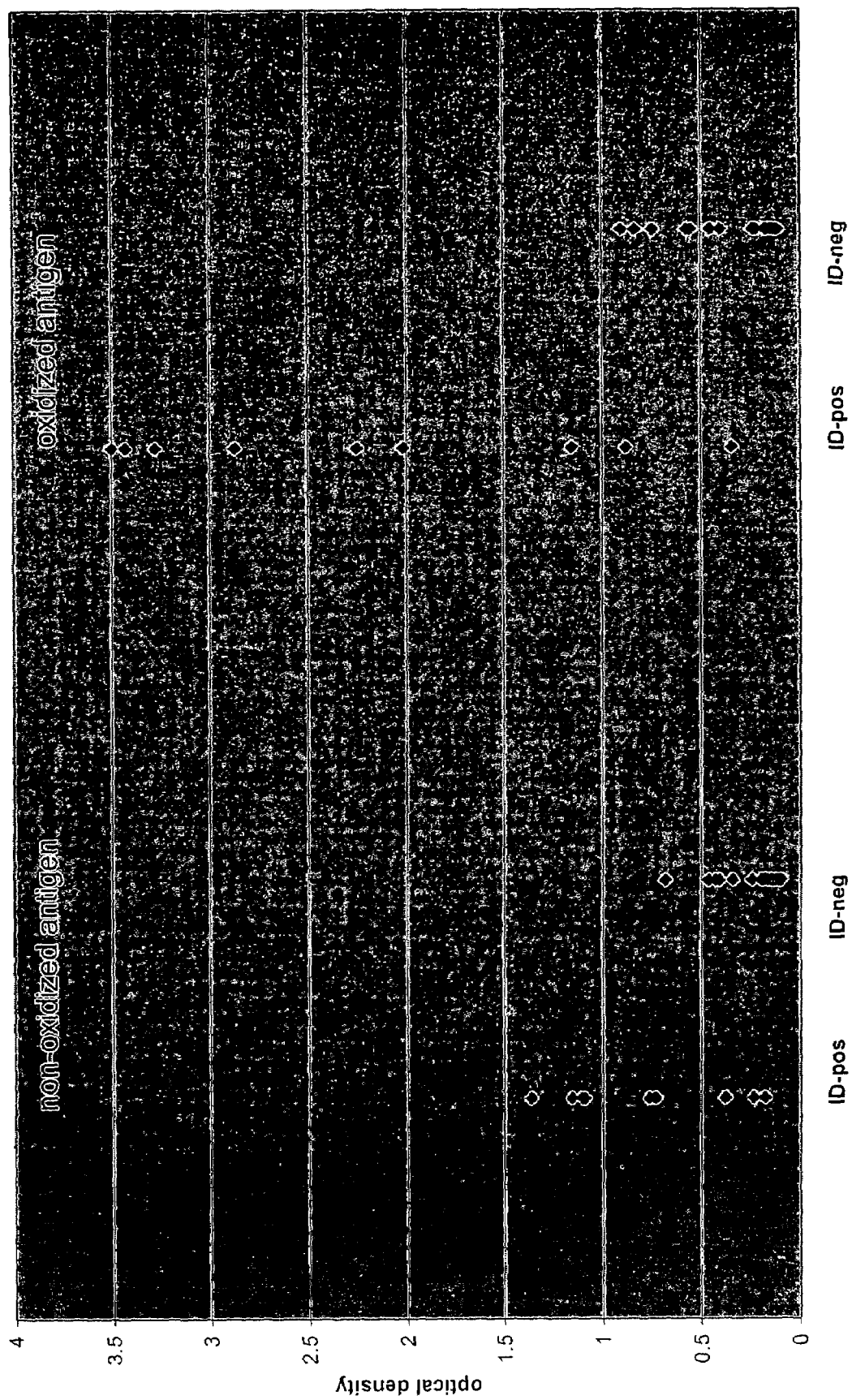
Figure 3. Aspergillus IgG ELISA

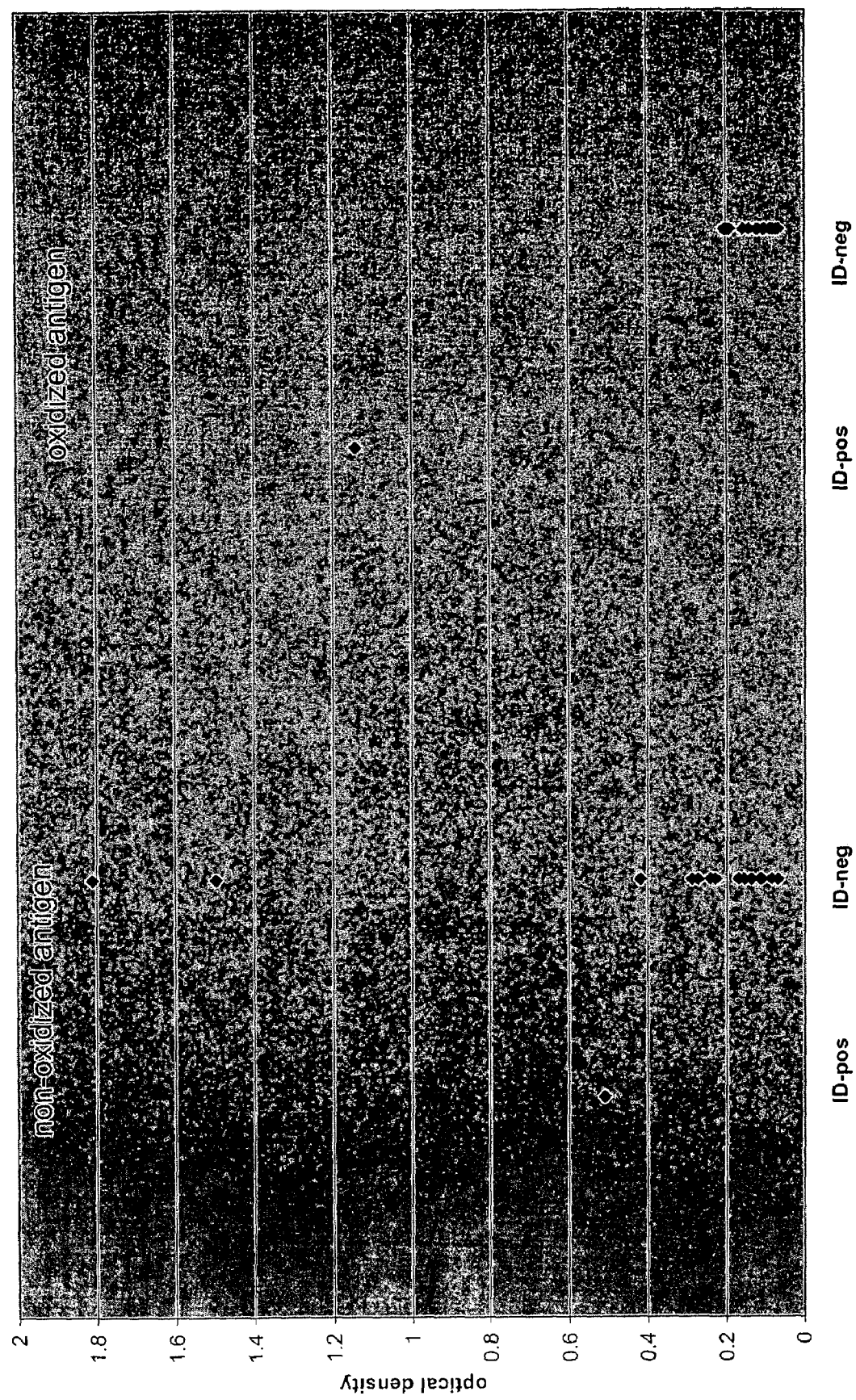
Figure 4. Blastomyces IgG ELISA

OXIDIZED FUNGAL ANTIGENS AND METHODS OF MAKING AND USING THEREOF

CROSS-REFERENCE TO RELATED APPLICATIONS

This application is a continuation in part of U.S. patent application Ser. No. 10/028,181, filed Dec. 21, 2001 now U.S. Pat No. 6,867,004. The disclosure of which is herein incorporated by reference in its entirety.

TECHNICAL FIELD

The present invention relates to oxidized fungal antigens and methods of making and using thereof. More particularly, the present invention provides a method for producing an oxidized fungal antigen in culture filtrate. The present invention also provides for the produced oxidized fungal antigens. Devices comprising such oxidized fungal antigens, methods for testing for fungal antibodies using the oxidized fungal antigens and methods for producing anti-fungal antibodies using oxidized fungal antigens are further provided. Antigen detection devices comprising anti-fungal antibodies raised against oxidized fungal antigens produced by the present methods are further provided.

BACKGROUND ART

Fungal infections are common in the United States, and are often associated with significant morbidity. For example, *Candida* species are the fourth most common organisms isolated from US hospital patients (Wenzel and Pfaller, *Infect. Control Hosp. Epidemiol.*, 12:523–524 (1991)). *Histoplasma capsulatum* and *Coccidioides immitis* causes, respectively, 250,000 and 100,000 new infections annually, and 10–40% of infected persons become symptomatic (Bullock, *Histoplasma capsulatum*, In: Principles and Practice of Infectious Diseases, G L Mandell et al. (eds.), Churchill Livingstone, New York, 1995, pp. 2340–2353 and 2365–2375; and Stevens, *N. Engl. J. Med.*, 332:1077–1082 (1995)). Individuals with symptomatic *C. immitis* infection miss an average of 35 days of school or work, and incur a total of $24 million in medical expenses annually.

Many fungi cause respiratory infections that are indistinguishable on the basis of symptoms. However, it is important to accurately determine which fungus is responsible for infection due to differences in treatment regimens and incidences of complications (Bullock, *Histoplasma capsulatum*, In: Principles and Practice of Infectious Diseases, G L Mandell et al. (eds.), Churchill Livingstone, New York, 1995, pp. 2340–2353 and 2365–2375; and Galgiani, *Ann. Intern. Med.*, 130:293–300 (1999)). Because culture and direct antigen detection are problematic, antibody detection plays an important role in the diagnosis and identification of fungal infections. The methods most commonly used to detect fungal antibodies include complement fixation (CF) and immunodiffusion (ID) (Zancope-Oliveira et al., *Clin. Diagn. Lab. Immunol.*, 1:90–93 (1994)). Both methods, however, have inherent drawbacks. ID detects antibodies to species-specific protein moieties, and is thus sensitive and highly specific; however, the assay takes 48 hours to perform, and appropriate interpretation requires highly skilled personnel. Although CF assays are highly sensitive, their performance is complex and labor-intensive, and they exhibit low specificity due to cross-reactive antibodies recognizing carbohydrate moieties common to several fungi (Zancope-Oliveira et al., *Clin. Diagn. Lab. Immunol.*, 1:90–93 (1994); and Yang et al., *Clin. Diagn. Lab. Immunol*, 4:19–22 (1997)). Enzyme-linked immunosorbent assays (ELISA) for the detection of fungal antibodies have also been described, but these assays exhibit low specificity due to the same cross-reactive antibodies at issue in CF assays (Zartarian et al., *Am. J. Clin. Pathol.*, 207:148–153 (1997); and Kaufman et al., *J. Clin. Microbiol.*, 33:618–619 (1995)).

During the last decade, investigators using a western blot assay system found that periodate oxidation of fungal antigen preparations inactivates the cross-reactive carbohydrate moieties but does not disturb the structural integrity of the protein moieties (Zancope-Oliveira et al., *Clin. Diagn. Lab. Immunol.*, 1:90–93 (1994); Zancope-Oliveira et al., *Clin. Diagn. Lab. Immunol.*, 1:563–568 (1994); and Pizzini et al., *Clin. Diagn. Lab. Immunol.*, 6:20–23 (1999)). Thus, utilization of oxidized fungal antigens markedly increased the specificity of the western blot assay for fungal antibodies, without affecting sensitivity. However, the western blot assay described therein is not practical for most medical laboratories; many complex steps are required, including antigen preparation, gel electrophoresis, electrotransfer to nitrocellulose membranes, assay performance, and blot interpretation. The antigen was a culture filtrate, 0.45 μm filtered, 20× concentrated by ultrafiltration, dialyzed against PBS, purified by ion exchange chromatography, 10× concentrated by ultrafiltration, and finally dialyzed against PBS. Oxidizing the antigen also included several labor intensive and potentially contaminating steps: 4 mg/mL antigen was exposed to periodate for 18 hours at 4° C., treated with glycerol for 15 minutes, treated with borohydrate for 2 hours, and finally dialyzed against water. Manufacturing the devices also included methods requiring sophisticated equipment and skilled technicians: denaturing the oxidized antigen with heat and mercaptoethanol, electrophoresing with a 4% stacking gel and 7.5% resolving gel, transferring the proteins to nitrocellulose paper, blocking with buffered milk and tween, drying the paper, and cutting the paper into strips, etc.

Although attempts to utilize periodate-treated fungal antigens for specific detection of fungal antibodies in an ELISA system have been reported, these attempts were only marginally successful (Fisher et al., *Mycroses*, 40:83–90 (1997)). Binding of *H. capsulatum* antibodies to oxidized *Blastomyces dermatitidis* antigens was reduced only by about 20% when compared to binding to non-oxidized *B. dermatitidis* antigens. This limited reduction in cross-reactivity may have been due to the use of highly purified (and thus extensively manipulated) fungal antigens, periodate oxidation after the antigens had adsorbed to the plastic surface, or the use of an insufficient concentration of periodate.

Therefore, there exists a need in the art for oxidized fungal antigens with more reduced cross-reactivity. The present invention addresses this and other related needs.

DISCLOSURE OF THE INVENTION

In one aspect, the present invention is directed to a method for producing a fungal antigen suitable for testing for an antibody to a fungus, the method comprising: a) providing a fungal antigen as a culture filtrate, the fungal antigen having not been purified by ion exchange chromatography or isoelectric focusing from the culture filtrate; and b) contacting the fungal antigen with an oxidizing agent to produce an oxidized fungal antigen suitable for testing for an antibody to the fungus. Devices comprising an oxidized fungal antigen, or a plurality of oxidized fungal antigens, produced by the above method, for testing for an anti-fungal antibody, or a plurality of anti-fungal antibodies, are also provided.

In another aspect, the present invention provides a method of testing an antibody to a fungus in a sample, the method comprising: a) providing a fungal antigen, b) simultaneously contacting the fungal antigen with an oxidizing agent to produce an oxidized fungal antigen and attaching the oxidized fungal antigen to a surface of a device suitable for testing an antibody to a fungus, wherein said oxidized fungal antigen is suitable for testing an antibody to the fungus; c) contacting a sample suspected of containing an antibody to a fungus with the oxidized fungal antigen produced in step b) under suitable conditions to allow binding of the antibody, if present in the sample, to the oxidized fungal antigen; and d) assessing binding between the antibody and the oxidized fungal antigen to determine the presence and/or amount of the antibody in the sample. In some embodiments, the fungal antigen is provided as a culture filtrate, the fungal antigen having not been purified by ion exchange chromatography or isoelectric focusing from the culture filtrate.

In yet another aspect, the present invention is directed to a method of testing for an antibody to a fungus in a sample, the method comprising: a) producing a fungal antigen suitable for testing for an antibody to a fungus, comprising providing a fungal antigen as a culture filtrate, the fungal antigen having not been purified by ion exchange chromatography or isoelectric focusing from the culture filtrate, and contacting the fungal antigen with an oxidizing agent to produce an oxidized fungal antigen suitable for testing for an antibody to the fungus; b) contacting a sample suspected of containing an antibody to a fungus with the oxidized fungal antigen produced in step a) under suitable conditions to allow binding of the antibody, if present in the sample, to the oxidized fungal antigen; and c) assessing binding between the antibody and the oxidized fungal antigen to determine the presence and/or amount of the antibody in the sample.

In still another aspect, the present invention is directed to a method for producing an antibody to a fungal antigen, the method comprising: a) producing a fungal antigen comprising providing a fungal antigen as a culture filtrate, the fungal antigen having not been purified by ion exchange chromatography or isoelectric focusing from the culture filtrate, and contacting the fungal antigen with an oxidizing agent to produce an oxidized fungal antigen; b) delivering, to a vertebrate, the oxidized fungal antigen, in an amount sufficient to induce detectable production of an antibody to the antigen; and c) recovering the antibody from the vertebrate.

In yet another aspect, the present invention is directed to a method for producing a monoclonal antibody to a fungal antigen, the method comprising: a) producing a fungal antigen comprising providing a fungal antigen as a culture filtrate, the fungal antigen having not been purified by ion exchange chromatography or isoelectric focusing from the culture filtrate, and contacting the fungal antigen with an oxidizing agent to produce an oxidized fungal antigen; b) delivering, to a vertebrate, the oxidized fungal antigen, in an amount sufficient to induce detectable production of an antibody to the antigen; c) removing at least a portion of antibody-producing cells from the vertebrate; d) immortalizing the removed antibody-producing cells; e) propagating the immortalized antibody-producing cells; and f) harvesting monoclonal antibody produced by the immortalized antibody-producing cells. Methods of testing for a fungal antigen in a sample using the produced antibodies are also provided.

BRIEF DESCRIPTION OF THE DRAWINGS

FIG. 1 illustrates a *Histoplasma capsulatum* IgG ELISA test using an oxidized and a non-oxidized antigen.

FIG. 2 illustrates a *Coccidioides immitis* IgG ELISA test using an oxidized and a non-oxidized antigen.

FIG. 3 illustrates a *Aspergillus fumigatus* IgG ELISA test using an oxidized and a non-oxidized antigen.

FIG. 4 illustrates a *Blastomyces dermatitidis* IgG ELISA test using an oxidized and a non-oxidized antigen.

MODES OF CARRYING OUT THE INVENTION

For clarity of disclosure, and not by way of limitation, the detailed description of the invention is divided into the subsections that follow.

A. Definitions

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, “a” or “an” means “at least one” or “one or more.”

As used herein, “fungus” refers to a division of eucaryotic organisms that grow in irregular masses, without roots, stems, or leaves, and are devoid of chlorophyll or other pigments capable of photosynthesis. Each organism (thallus) is unicellular to filamentous, and possesses branched somatic structures (hyphae) surrounded by cell walls containing glucan or chitin or both, and containing true nuclei.

As used herein, “culture” refers to a growth of living cells or microorganisms, e.g., fungi, in a controlled artificial environment.

As used herein, “filtration” refers to a process of separating particulate matter from a fluid, such as air or liquid, by passing the fluid carrier through a medium that will not pass the particulates.

As used herein, “filtrate” refers to a fluid, e.g., a liquid, that passes through the medium in filtration.

As used herein, “a fungal antigen as a culture filtrate” refers to a culture filtrate of a fungus containing the fungal antigenic substances. The culture filtrate can contain secreted extracellular fungal antigenic substances derived from supernatant of the fungal culture. Alternatively, culture filtrate can contain intracellular fungal antigenic substances derived from solution or suspension of disrupted fungal cells.

As used herein, “fungal antigen having (or has) not been purified” means that a particular fungal antigen (or a group of fungal antigens) has not been isolated or purified from other antigenic substances in the culture filtrate by any isolation or purification methods. However, the fungal antigen existing in the culture filtrate can be concentrated or diluted along with the concentration or dilution of the culture filtrate.

As used herein, "fungal antigen having not been purified by ion exchange chromatography or isoelectric focusing from the culture filtrate" means that a particular fungal antigen (or a group of fungal antigens) has not been isolated or purified from other antigenic substances in the culture filtrate by ion exchange chromatography or isoelectric focusing. However, the fungal antigen existing in the culture filtrate can be concentrated or diluted along with the concentration or dilution of the culture filtrate, or can be isolated or purified from other antigenic substances in the culture filtrate by any isolation or purification methods other than ion exchange chromatography and isoelectric focusing.

As used herein, an "oxidizing agent (or oxidant)" refers to an agent that accepts electrons in an oxidation-reduction reaction.

As used herein the term "assessing (or assessed)" is intended to include quantitative and qualitative determination of the identity of a moiety, e.g., an antigen, an antibody or an antigen-antibody complex, present in the sample, and also of obtaining an index, ratio, percentage, visual or other value indicative of the identity of a moiety in the sample. Assessment may be direct or indirect.

As used herein, "sample" refers to anything which may contain a fungal antigen or antibody to be tested by the present devices and/or methods. The sample may be a biological sample, such as a biological fluid or a biological tissue. Examples of biological fluids include urine, blood, plasma, serum, saliva, semen, stool, sputum, cerebral spinal fluid, tears, mucus, amniotic fluid or the like. Biological tissues are aggregates of cells, usually of a particular kind together with their intercellular substance that form one of the structural materials of a human, animal, plant, bacterial, fungal or viral structure, including connective, epithelium, muscle and nerve tissues. Examples of biological tissues also include organs, tumors, lymph nodes, arteries and individual cell(s). The sample may also be a fungal culture, e.g., a fungal culture derived from a biological sample.

As used herein, a "liquid (fluid) sample" refers to a sample that naturally exists as a liquid or fluid, e.g., a biological fluid. A "liquid sample" also refers to a sample that naturally exists in a non-liquid status, e.g., solid or gas, but is prepared as a liquid, fluid, solution or suspension containing the solid or gas sample material. For example, a liquid sample can encompass a liquid, fluid, solution or suspension containing a biological tissue.

B. Methods for Producing Oxidized Fungal Antigen

In one aspect, the present invention is directed to a method for producing a fungal antigen suitable for testing for an antibody to a fungus, the method comprising: a) providing a fungal antigen; and b) contacting the fungal antigen with an oxidizing agent to produce an oxidized fungal antigen suitable for testing for an antibody to the fungus. In some embodiments, the fungal antigen is provided as a culture filtrate, the fungal antigen having not been purified by ion exchange chromatography or isoelectric focusing from the culture filtrate.

The present methods can be used to produce an oxidized fungal antigen from any fungal genus or species. The oxidized antigens, while being reactive to antibodies to the fungus from which the fungal antigen is derived, may be reactive to antibodies to the fungus of other related genus or species. Preferably, the methods will be controlled to produce oxidized fungal antigens that are able to distinguish among different fungal genus. More preferably, the methods will be controlled to produce oxidized fungal antigens that are able to distinguish among different fungal species within the same genus.

Fungi can be generally described as follows (Brock and Madigan, *Biology of Microorganisms* (6th Ed.), Prentice Hall, Englewood Cliffs, N.J. 07632 (1991), pp. 817–818). In contrast to the algae, the fungi lack chlorophyll. Fungi can be differentiated from bacteria by the fact that fungal cells are usually much larger and contain a nucleus, vacuoles, and mitochondria, typical of eucaryotic cells. Although the fungi are a large and diverse group of eucaryotic microorganisms, three groups of fungi have major practical importance: the molds, yeasts, and mushrooms.

The habitats of fungi are quite diverse. Some are aquatic, living primarily in fresh water, and a few marine fungi are also known. Most fungi, however, have terrestrial habitats, in soil or on dead plant matter, and these types often play crucial roles in the mineralization of organic carbon in nature. A large number of fungi are parasites of terrestrial plants. Indeed, fungi cause the majority of economically significant diseases of crop plants (see Table 1). A few fungi are parasitic on animals, including humans, although in general fungi are less significant as animal pathogens than are bacteria and viruses.

TABLE 1

Classification and major properties of fungi

| Group | Common name | Hyphae | Typical representatives | Type of sexual spore | Habitats | Common diseases |
|---|---|---|---|---|---|---|
| Ascomycetes | Sac fungi | Septate | *Neurospora*, *Saccharomyces*, *Morchella* (morels) | Ascospore | Soil, decaying plant material | Dutch elm, chestnut blight, ergot, rots |
| Basidiomycetes | Club fungi, mushrooms | Septate | *Amanita* (poisonous mushroom), *Agaricus* (edible mushroom) | Basidiospore | Soil, decaying plant material | Black stem, wheat rust, corn smut |
| Zygomycetes | Bread molds | Coenocytic | *Mucor*, *Rhizopus* (common bread mold) | Zygospore | Soil, decaying plant material | Food spoilage; rarely involved in parasitic disease |

TABLE 1-continued

Classification and major properties of fungi

| Group | Common name | Hyphae | Typical representatives | Type of sexual spore | Habitats | Common diseases |
|---|---|---|---|---|---|---|
| Oomycetes | Water molds | Coenocytic | *Allomyces* | Oospore | Aquatic | Potato blight, certain fish diseases |
| Deuteromycetes | Fungi imperfecti | Septate | *Penicillium*, *Aspergillus* | None | Soil, decaying plant material, surfaces of animal bodies | Plant wilt, fungal infections of animals such as ringworm, athlete's foot, and other dermatomycoses |

All fungi are organotrophs. Lacking chlorophyll, they of course cannot photosynthesize, and the group also lacks lithotrophic forms. When compared to the bacteria, the fungi in general have fairly simple nutritional requirements, and their metabolic and biosynthetic processes are not particularly diverse or unusual. It is in their morphological properties and in their sexual life cycles that the fungi exhibit considerable diversity; hence it is on the basis of these characteristics that the fungi are classified.

In a specific embodiment, the present method is used to produce an oxidized fungal antigen from a mitosporic Trichocomaceae, an Onygenaceae or a mitosporic Onygenale. In another specific embodiment, the present method is used to produce an oxidized fungal antigen from *Aspergillus*, e.g., *Aspergillus fumigatus*, *Blastomyces* (*Ajellomyces*), e.g., *Blastomyces dermatitidis*, *Coccidioides*, e.g., *Coccidioides immitis*, *Histoplasma*, e.g., *Histoplasma capsulatum* and *Histoplasma duboifii*, *Candida*, e.g., *Candida albicans* and *Cyrptococcus*, e.g., *Cyrptococcus neoformans*.

In still another specific embodiment, the present method is used to produce an oxidized fungal antigen from a fungal antigen not derived from *Aspergillus*, e.g., *Aspergillus fumigatus*, *Blastomyces* (*Ajellomyces*), e.g., *Blastomyces dermatitidis*, *Coccidioides*, e.g., *Coccidioides immitis*, *Histoplasma*, e.g., *Histoplasma capsulatum* and *Histoplasma duboifii*, *Candida*, e.g., *Candida albicans* and *Cyrptococcus*, e.g., *Cyrptococcus neoformans*.

In some embodiments, the fungal antigen to be oxidized should not have been purified by ion exchange chromatography or isoelectric focusing from the culture filtrate. However, the fungal antigen to be oxidized can be concentrated or diluted along with the concentration or dilution of the culture filtrate, or can be isolated or purified from other antigenic substances in the culture filtrate by any isolation or purification methods other than ion exchange chromatography and isoelectric focusing. For example, the fungal antigen can be isolated or purified by any chromatographic methods other than ion exchange chromatography or any electrophoresis other than isoelectric focusing, as well as other types of isolation or purification methods such as centrifugation or organic-aqueous phase separations. In a specific embodiment, the fungal antigen to be oxidized has not been purified from the culture filtrate prior to the oxidation step.

The present methods can comprise additional steps. For example, the present methods can further comprise a step of concentrating the culture filtrate. The concentrating step can be conducted prior to, concurrently with and/or subsequent to the oxidation step. Preferably, the concentrating step is conducted prior to the oxidation step. In another example, the present methods can further comprise a step of enzymatically deglycosylating the fungal antigen. Any suitable deglycosylating enzymes can be used, e.g., Endo H, PNGase F, O-glycancase, etc. The enzymatic deglycosylation step can be conducted prior to, concurrently with and/or subsequent to the oxidation step. Preferably, enzymatic deglycosylation step is conducted prior to the oxidation step.

Any suitable oxidizing agent can be used in the present methods. Exemplary oxidizing agents include hydrogen peroxide ($H_2O_2$), ozone ($O_3$), polyatomic oxygen $O_7$, polyatomic oxygen $O_8$, $NaIO_4$, potassium peroxymonosulfate (oxone) (Wozniak et al., *Bioorg. Med. Chem. Lett.*, 8(19): 2641–6 (1998)), D,L-S-methyllipoic acid methyl ester (Pan and Jordan, *Biochemistry*, 37(5):1357–64 (1998)), tertiary butyl hydroperoxide (Tarin et al., *Mol. Hum. Reprod.*, 2(12): 895–901 (1996)), menadione (Santini et al., *Free Radic. Biol. Med.*, 20(7):915–24 (1996)), diamide (Bosin and Kasper, *J. Biochem. Toxicol.*, 7(3):139–45 (1992)), iodogen (Saha et al., *Int. J. Rad. Appl. Instrum.*, 16(4):431–3 (1989)), N-bromosuccinimide (Sinn et al., *Anal. Biochem.*, 170(1): 186–92 (1988)), omeprazole (Im et al., *J Biol. Chem.*, 260(8):4591–7 (1985)), and N-ethylmaleimide (Marzulli et al., *Boll. Soc. Ital. Biol. Sper.*, 61(1):121–7 (1985)).

In a specific embodiment, the oxidizing agent used in the present methods inactivates the cross-reactive carbohydrate moiety of the fungal antigen but does not disturb the structural integrity or antigenicity of the non-carbohydrate moieties. For example, when the fungal antigen to be oxidized is a glycosylated protein or peptide, the oxidizing agent inactivates the cross-reactive carbohydrate moiety of the fungal antigen but does not disturb the structural integrity or antigenicity of the proteineous or peptidyl moiety.

In a preferred embodiment, the oxidizing agent used in the present methods is periodate (or periodic acid), which has a molecular formula $H_5IO_6$. Suitable salts, esters or other derivatives of periodate that retain periodate's oxidizing activity, e.g., sodium meta-periodate (Sigma). can also be used. Periodate or its salts, esters or other derivatives thereof can be produced by methods known in the art. For example, periodate can be prepared by electrolytic oxidation of iodic acid or from barium periodate and nitric acid (Willard, *Inorg. Syn.* 1, 172 (1939); Chemistry of periodic acid and periodates; H. Siebert, *Fortschr. Chem. Forsch.* 8, 470 (1967); Periodic acid and periodates in organic and bioorganic chemistry; A. J. Fatiadi, *Synthesis* 1974, 229; and G. Dryhurst, *Periodate Oxidation of Diol and Other Functional Groups* (Pergamon Press, New York, 1970)). Alternatively, Periodate or its salts, esters or other derivatives thereof can be obtained commercially, e.g., from Sigma.

The oxidation step can be conducted under any suitable conditions depending on a number of factors such as the fungal antigen to be oxidized, the oxidizing agent to be used, the properties of the culture filtrate, the degree of concentration and/or dilution of the culture filtrate and the presence or absence of any enzymatic deglycosylation. Generally, the concentration of the oxidizing agent can be in a wide range, e.g., from 0.01 M to about 0.1 M if periodate is used. The oxidation step can be conducted at any suitable temperature, e.g., from about 4° C. to an ambient temperature, e.g., from about 25° C. to about 30° C. The incubation time can also have a wide range, e.g., from about 1 hour to about 20 hours. When periodate is used, oxidation step is preferably conducted at about 25° C. for about 1–3 hours.

In some embodiments, the present method can further comprise a step of attaching the oxidized fungal antigen to a surface of a device suitable for testing for an antibody to a fungus. In other embodiments, the present method comprises the simultaneous oxidation of the fungal antigen and attachment of the oxidized fungal antigen to the surface of the device. Any suitable device can be used such as a microtiter plate, a glass slide, a nitrocellulose membrane, a latex bead, a cell, a test tube, a plastic bead, a colloidal gold particle, a colored particle, a magnetic bead and a quantum dot. Preferably, a microtiter plate is used.

Fungal antigens, suitable for testing for an antibody to a fungus, which are produced by the present methods are also provided. Devices, suitable for testing for an antibody to a fungus, which are produced by the present methods are further provided. In a preferred embodiment, a device for simultaneously testing for a plurality of fungal antibodies is provided, the device comprising a plurality of fungal antigens produced by the present methods attached to a surface of the device suitable for testing for an antibody to a fungus, wherein the plurality of fungal antigens are attached to areas of the surface that are physically distinct from each other. Any suitable device can be used. In one example, the device comprises an immunoblot and wherein the plurality of fungal antigens are attached to separate stripes in the immunoblot. In another example, the device comprises an IFA well and wherein the plurality of fungal antigens are attached to different spots within the IFA well. In still another example, the device comprises an IFA slide and wherein the plurality of fungal antigens are attached to different wells of the IFA slide. Other exemplary devices include a microtiter plate, a glass slide, a nitrocellulose membrane, a latex bead, a cell, a test tube, a plastic bead, a colloidal gold particle, a colored particle, a magnetic bead and a quantum dot.

C. Methods of Testing for an Antibody to a Fungus

In one aspect, the present invention is directed to a method of testing for an antibody to a fungus in a sample, the method comprising: a) producing a fungal antigen suitable for testing for an antibody to a fungus, comprising providing a fungal antigen as a culture filtrate, the fungal antigen having not been purified by ion exchange chromatography or isoelectric focusing from the culture filtrate, and contacting the fungal antigen with an oxidizing agent to produce an oxidized fungal antigen suitable for testing for an antibody to the fungus; b) contacting a sample suspected of containing an antibody to a fungus with the oxidized fungal antigen produced in step a) under suitable conditions to allow binding of the antibody, if present in the sample, to the oxidized fungal antigen; and c) assessing binding between the antibody and the oxidized fungal antigen to determine the presence and/or amount of the antibody in the sample.

In another aspect, the present invention is directed to a method of testing an antibody to a fungus in a sample, the method comprising: a) providing a fungal antigen; b) simultaneously contacting the fungal antigen with an oxidizing agent to produce an oxidized fungal antigen, wherein said oxidized fungal antigen is suitable for testing an antibody to the fungus, and attaching the oxidized fungal antigen to a surface of a device suitable for testing said antibody to the fungus; c) contacting a sample suspected of containing an antibody to a fungus with the oxidized fungal antigen produced in step b) under suitable conditions to allow binding of the antibody, if present in the sample, to the oxidized fungal antigen; and d) assessing binding between the antibody and the oxidized fungal antigen to determine the presence and/or amount of the antibody in the sample.

The present methods can be used to test for an antibody to any fungus in a sample, including any fungus described in the above Section B. Preferably, the antibody to be tested is to a pathogenic fungus such as *Aspergillus*, e.g., *Aspergillus fumigatus*, *Blastomyces* (*Ajellomyces*), e.g., *Blastomyces dermatitidis*, *Coccidioides*, e.g., *Coccidioides immitis*, *Blastocystis*, e.g., *Blastocystis hominis*, *Histoplasma*, e.g., *Histoplasma capsulatum* and *Candida*, e.g., *Candida albicans* and *Candida neoformans*.

The present methods can be used to test any sample. Preferably, the sample to be tested is a clinical sample including human and veterinary clinical samples. More preferably, the sample to be tested is a human clinical sample.

The oxidized fungal antigens to be used in the present test methods are produced as described in the above Section B. Preferably, the fungal antigen to be oxidized has not been purified from the culture filtrate. Also, preferably, the oxidizing agent to be used is periodate.

The present test methods can be conducted in liquid or solid phase. In specific embodiment, the present test method is conducted in a solid phase the method further comprises a step of attaching the oxidized fungal antigen to a surface of a device suitable for testing for an antibody to a fungus before contacting the antigen with the sample.

The binding between the antibody and the oxidized fungal antigen can be assessed by any suitable assay formats. For example, the binding between the antibody and the oxidized fungal antigen can be assessed by a sandwich or competitive assay format. In another example, the binding between the antibody and the oxidized fungal antigen can be assessed by an enzyme-linked immunosorbent assay (ELISA), immunoblotting, immunoprecipitation, radioimmunoassay (RIA), immunostaining, latex agglutination, indirect hemagglutination assay (IHA), complement fixation, indirect immunofluorescent assay (IFA), nephelometry, flow cytometry assay, chemiluminescence assay, lateral flow immunoassay, u-capture assay, inhibition assay or avidity assay (Manual of Clinical Laboratory Immunology, N R Rose, E Conway de Macario, J D Folds, H C Lane, R M Nakamura, eds. ASM Press, Washington D.C., 1997). Preferably, the binding between the antibody and the oxidized fungal antigen is assessed by an ELISA format.

The present assay method can be conducted for prognosis, diagnosis and/or monitoring treatment of pathogenic fungal infection, e.g., histoplasmosis caused by *Histoplasma capsulatum* infection, blastomycosis caused by *Blastomyces dermatitidis* infection, candidasis caused by *Candida albicans* or *Candida neoformans* infection, etc.

D. Methods for Producing an Antibody to an Fungal Antigen

In still another aspect, the present invention is directed to a method for producing an antibody to a fungal antigen, the method comprising: a) producing a fungal antigen comprising providing a fungal antigen as a culture filtrate, the fungal antigen having not been purified by ion exchange chromatography or isoelectric focusing from the culture filtrate, and contacting the fungal antigen with an oxidizing agent to produce an oxidized fungal antigen; b) delivering, to a vertebrate or tissue culture, the oxidized fungal antigen, in an amount sufficient to induce detectable production of an antibody to the antigen; and c) recovering the antibody from the vertebrate or tissue culture.

The oxidized fungal antigens to be used in the present antibody producing methods are produced as described in the above Section B. Preferably, the fungal antigen to be oxidized has not been purified from the culture filtrate. Also, preferably, the oxidizing agent to be used is periodate.

Any suitable non-human mammal can be used in the present methods. For example, mouse, rabbit and goat can be used.

The antibody to a fungal antigen, e.g., a polyclonal antiserum, which is produced by the present method is also provided.

In yet another aspect, the present invention is directed to a method for producing a monoclonal antibody to an fungal antigen, the method comprising: a) producing a fungal antigen comprising providing a fungal antigen as a culture filtrate, the fungal antigen having not been purified by ion exchange chromatography or isoelectric focusing from the culture filtrate, and contacting the fungal antigen with an oxidizing agent to produce an oxidized fungal antigen; b) delivering, to a vertebrate or tissue culture, the oxidized fungal antigen, in an amount sufficient to induce detectable production of an antibody to the antigen; c) removing at least a portion of antibody-producing cells from the vertebrate or tissue culture; d) immortalizing the removed antibody-producing cells; e) propagating the immortalized antibody-producing cells; and f) harvesting monoclonal antibody produced by the immortalized antibody-producing cells. Methods of testing for a fungal antigen in a sample using the produced monoclonal antibodies are also provided.

The oxidized fungal antigens to be used in the present antibody producing methods are produced as described in the above Section B. Preferably, the fungal antigen to be oxidized has not been purified from the culture filtrate. Also, preferably, the oxidizing agent to be used is periodate.

Any suitable non-human mammal can be used in the present methods. For example, mouse, rabbit and goat can be used.

A monoclonal antibody to a fungal antigen, which is produced by the present method is also provided.

A hybridoma capable of producing a monoclonal antibody to a fungal antigen, which is produced by steps a)–d) of the present method is further provided.

The oxidized fungal antigens can be delivered to a vertebrate or non-human mammal by any methods known in the art (See e.g., Coligan et al. (Ed.), CURRENT PROTOCOLS IN IMMUNOLOGY, 2.II Production of Antibodies, John Wiley & Sons, Inc. (2000)).

The oxidized fungal antigens can be delivered to the interstitial space of tissues of the animal body, including those of muscle, skin, brain, lung, liver, spleen, bone marrow, thymus, heart lymph, blood, bone, cartilage, pancreas, kidney, gall bladder, stomach, intestine, testis, ovary, uterus, rectum, nervous system, eye, gland, and connective tissue. Interstitial space of the tissues comprises the intercellular, fluid, mucopolysaccharide matrix among the reticular fibers or organ tissues, elastic fibers in the walls of vessels or chambers, collagen fibers of fibrous tissues, or that same matrix within connective tissue ensheathing muscle cells or in the lacunae of bone. It is similarly the space occupied by the plasma of the circulation of the lymph fluid of the lymphatic channels.

The oxidized fungal antigens can be conveniently delivered by injection into the tissues comprising these cells. They are preferably delivered to persistent, non-dividing cells which are differentiated, although delivery can be achieved in non-differentiated or less completely differentiated cells, such as, for example, stem cells of blood or skin fibroblasts.

In a specific embodiment, the oxidized fungal antigen is delivered directly to a tissue of the animals. Preferably, the oxidized fungal antigen is delivered directly to muscle, skin or mucous membrane. In one example, the oxidized fungal antigen can be delivered directly to a tissue of the animal by injection, by gene gun technology or by lipid mediated delivery technology. The injection can be conducted via a needle or other injection devices. The gene gun technology is disclosed in U.S. Pat. No. 5,302,509 and the lipid mediated delivery technology is disclosed in U.S. Pat. No. 5,703,055, the contents of which are incorporated herein by reference.

In still another specific embodiment, the oxidized fungal antigen is delivered to a cell of the animal and the cell containing the oxidized fungal antigen is delivered to a suitable tissue of the animal. Preferably, the oxidized fungal antigen is delivered to a blood cell of an animal. More preferably, the oxidized fungal antigen is delivered to a spleen B cell of an animal.

The anti-fungal antibodies, whether polyclonal or monoclonal, that are produced by the above methods can be used in testing for a fungal antigen in a sample. In one specific embodiment, the present invention is directed to a method of testing for a fungal antigen in a sample, the method comprising: a) providing an anti-fungal polyclonal antiserum produced by the above antibody producing method; b) contacting a sample suspected of containing a fungal antigen with the polyclonal antiserum under suitable conditions to allow binding of the fungal antigen, if present in the sample, to the polyclonal antiserum; and c) assessing binding between the fungal antigen and the polyclonal antiserum to determine the presence and/or amount of the fungal antigen in the sample.

In another specific embodiment, the present invention is directed to a method of testing for a fungal antigen in a sample, the method comprising: a) providing an anti-fungal antigen monoclonal antibody produced by the above antibody producing method; b) contacting a sample suspected of containing a fungal antigen with the monoclonal antibody under suitable conditions to allow binding of the fungal antigen, if present in the sample, to the monoclonal antibody; and c) assessing binding between the fungal antigen and the monoclonal antibody to determine the presence and/or amount of the fungal antigen in the sample.

E. Exemplary Embodiments

In exemplary embodiments of the present invention, oxidized preparations of crude fungal antigens are used in an ELISA format, resulting in the sensitive and specific detection of fungal antibodies. The fungal antigens can be oxidized during a short (2-hour) incubation with periodate, then further diluted with coating buffer and allowed to adsorb to polystyrene microtiter wells. Alternatively, the fungal antigens are oxidized and allowed to adsorb to the polystyrene microtiter wells simultaneously. ELISA performance using these coated microtiter wells is complete within 4 hours, thus providing sensitive and specific results more quickly and easily than ID and western blot assays.

Preparation of Antigen-Coated Microtiter Wells

A fungal antigen preparation, designed for use in ID assays, is purchased from a commercial source. The protein concentration of the antigen preparation is determined by protein-dye binding (Bradford) assay. The fungal antigen is then diluted to a final protein concentration of about 10–50 micrograms per milliliter (ug/mL) in 0.05M sodium acetate buffer (adjusted to pH 5.5 using 10% acetic acid) containing about 0.02M–0.10M sodium meta-periodate. After a short incubation period (1–3 hours) at room temperature, during which hydroxyl groups of the fungal antigen carbohydrate moieties are cleaved and converted to aldehydes (i.e., become oxidized), the oxidized fungal antigen preparation is diluted approximately 20-fold with phosphate buffered saline (PBS), pH 7.4. This diluted fungal antigen is then added to polystyrene microtiter wells at a volume of 0.1 mL per well. The microtiter wells are covered with plastic adhesive tape and incubated in the refrigerator (4–8° C.) for 14–18 hours. During this incubation, fungal antigen protein moieties attach to the polystyrene through hydrophobic interactions. After incubation, the solution is discarded from the microtiter wells, now bearing attached oxidized fungal antigen. All microtiter wells then receive 0.2 mL of PBS containing a blocking agent, such as bovine serun albumin (BSA), and a stabilizing agent, such as trehalose. The blocking agent attaches to any polystyrene binding sites that are left exposed after the incubation with oxidized fungal antigen. This step reduces the nonspecific attachment of antibody molecules not directed toward the specific antigens, and also reduces nonspecific adsorption of the conjugate during the color generation step. After 2 hours at room temperature, the blocking solution is discarded from the microtiter wells. The microtiter plates are air-dried at room temperature, then placed inside a plastic pouch, and the pouch heat-sealed. Sealed pouches containing microtiter plates coated with fungal antigens are stored in the refrigerator until use in the ELISA.

A fungal antigen preparation, designed for use in ID assays, is purchased from a commercial source. The protein concentration of the antigen preparation is determined by protein-dye binding (Bradford) assay. The fungal antigen is then diluted to a final plate coating concentration of about 0.5–10 micrograms per milliliter (ug/mL) in 0.05M sodium acetate buffer (adjusted to pH 5.5 using 10% acetic acid) containg approximately 0.02 M–0.10 M sodium metaperiodate. This diluted fungal antigen solution containing sodium metaperiodate is then added to polystyrene microtiter wells at a volume of 0.1 mL per well. The microtiter wells are covered with plastic adhesive tape and incubated in the refrigerator (4–8° C.) for 14–18 hours. During this incubation, fungal antigen protein moieties attach to the polystyrene through hydrophobic interactions. After incubation, the solution is discarded from the microtiter wells, now bearing attached oxidized fungal antigen. All microtiter wells then receive 0.2 mL of PBS containing a blocking agent, such as bovine serum albumin (BSA), and a stabilizing agent, such as trehalose. The blocking agent attaches to any polystyrene binding sites that are left exposed after the incubation with oxidized fungal antigen. This step reduces the nonspecific attachment of antibody molecules not directed toward the specific antigens, and also reduces nonspecific adsorption of the conjugate during the color generation step. After 2 hours at room temperature, the blocking solution is discarded from the microtiter wells. The microtiter plates are air-dried at room temperature, then placed inside a plastic pouch, and the pouch heat-sealed. Sealed pouches containing microtiter plates coated with fungal antigens are stored in the refrigerator until use in the ELISA.

ELISA Performance

Antigen-coated microtiter well plates are removed from the refrigerator and allowed to warm to room temperature. The wells are then filled with PBS containing a mild detergent such as Tween 20 (PBST), and after 5 minutes this PBST is discarded. This wash step ensures that all antigen and blocking solution proteins have been removed; in addition, the small amount of detergent helps to reduce bubble formation in subsequent steps. Serum samples are diluted in PBST that contains the same protein that is used as a blocking agent (such as BSA). About 0.1 mL of each diluted serum is added to an assigned microtiter well. The microtiter plate is then covered with adhesive tape and incubated about 1.5 hours at room temperature. During this incubation period, any serum antibodies directed to the antigen that is attached to the microtiter well will bind to the antigen. At the end of this incubation, the liquid material is discarded from all the wells. About 0.25 mL of PBST is then added to each well, and this fluid is then discarded; this wash step is repeated three times. This washing procedure ensures that non-attached serum components are removed from the microtiter well. About 0.1 mL of a conjugate diluted in PBST is then added to each well. This conjugate is a commercially-available, species-specific, anti-immunoglobulin with an enzyme chemically linked (conjugated) to it. The enzyme used is selected based on its ability to react with a substrate to produce a colored compound. A typical conjugate would be goat anti-human IgG tagged with horseradish peroxidase. This conjugate will bind to any IgG antibodies in the serum that attached to the antigen attached to the microtiter well. Following another series of washes to remove any unbound conjugate, enzyme substrate is added to each microtiter well. A typical substrate would be tetramethylbenzidine (TMB) and hydrogen peroxide; in the presence of horseradish peroxidase, this substrate produces a bluish purple color. Thus, color only develops when a "sandwich" consisting of plastic-bound antigen, serum-derived antibody, and enzyme-tagged conjugate has been built up; if the serum contains no antigen-specific antibody molecules, then the enzyme-tagged conjugate will not bind, and no color will develop because the enzyme is absent from the system. After a defined amount of time, a solution of dilute hydrochloric acid, or some other acid, is added to lower the pH of the solution in the wells. At a lower pH, the bluish purple color changes to a yellow color. The absorbance (also called optical density) of the yellow color is then quantitated using a spectrophotometric instrument. The microtiter well plate is placed inside the instrument, and the optical density for each well (i.e., each sample) is measured at a light wavelength of 450 nanometers. The optical density value is directly proportional to the intensity of the yellow color, which in turn is directly proportional to the amount of antigen-specific IgG antibody bound to the well.

EXAMPLE 1

Detection of IgG Antibodies Recognizing
*Histoplasma capsulatum*

*Histoplasma capsulatum* antigen (culture filtrate containing both H and M antigens) intended for use in ID assays was purchased from a commercial source, and adjusted to 20 ug/mL in sodium acetate buffer containing 0.05M periodate (hereafter referred to as oxidized antigen). For comparative purposes, a duplicate antigen suspension in sodium acetate buffer without periodate was prepared (hereafter referred to as nonoxidized antigen). After 2 hours at room temperature, the antigen preparations were diluted 20-fold in PBS to a final concentration of 1 ug/mL, then added to microtiter wells (0.1 mL per well). Thus, some microtiter wells received oxidized *Histoplasma* antigen, whereas other wells received nonoxidized *Histoplasma* antigen. After an overnight incubation in the refrigerator, the *Histoplasma* antigen preparations (oxidized or nonoxidized) were discarded from the wells, and PBS containing 0.1% (w/v) BSA and 5% (w/v) trehalose was added to the wells as blocking agent. After 2 hours at room temperature, the blocking agent was discarded, and the plates were then air-dried at room temperature for 2 hours. After pouching, the plates were stored in the refrigerator.

On the day of assay, *Histoplasma*-coated microtiter wells (some coated with oxidized antigen, others coated with nonoxidized antigen) were allowed to come to room temperature. During this step, 80 serum samples previously tested for *Histoplasma* antibodies by ID (16 positive, 64 negative) were diluted 1:400 in sample dilution buffer (PBST containing BSA). Once the wells had reached room temperature (approximately 1 hour), they were washed once with PBST, and the wash solution discarded. Diluted serum samples were then added to duplicate microtiter wells (one containing oxidized *Histoplasma* antigen, the other containing nonoxidized *Histoplasma* antigen). The microtiter wells were covered with adhesive tape and incubated at room temperature for 1.5 hours. Following 4 washes with PBST, each well then received 0.1 mL of horseradish peroxidase-conjugated goat anti-human IgG (diluted 1:10000 in PBST), and incubation was continued for 1 hour at room temperature. Following another series of 4 washes, each well then received 0.1 mL of tetra-methylbenzidine; after 10 minutes at room temperature, the reaction was stopped by the addition of 0.1N hydrochloric acid. The optical density was measured at 450 nM using a spectrophotometric ELISA reader.

FIG. 1 presents the optical density (OD) values obtained following incubation of ID-positive and ID-negative serum samples in microtiter wells coated with nonoxidized and oxidized *Histoplasma* antigen. When using nonoxidized *Histoplasma* antigen as substrate, the distribution of OD values for the ID-negative serum group was similar to that observed for the ID-positive serum group. In contrast, when using the oxidized *Histoplasma* antigen as substrate, the distribution of values for the ID-negative serum group was markedly different from the distribution of values for the ID-positive serum group. When using the oxidized antigen, 16 of 16 (100%) ID-positive serum samples exhibited OD values >1.45, whereas only 4 of 64 (6%) ID-negative serum samples exhibited OD values >1.45. Expressed another way, the *Histoplasma* IgG assay using oxidized *Histoplasma* antigen as substrate was 100% sensitive and 94% specific (see Table 2) using an OD cutoff value of 1.45.

TABLE 2

Specificities of fungal IgG ELISAs using oxidized versus nonoxidized antigens under conditions giving the same sensitivities

| ELISA | Antigen type | Cutoff OD | Sensitivity (%) | Specificity (%) |
|---|---|---|---|---|
| Histoplasma | Oxidized | 1.45 | 100 | 94 |
| IgG | Nonoxidized | 0.50 | 100 | 25 |
| Coccidioides | Oxidized | 1.00 | 90 | 97 |
| IgG | Nonoxidized | 0.22 | 90 | 28 |

TABLE 2-continued

Specificities of fungal IgG ELISAs using oxidized versus nonoxidized antigens under conditions giving the same sensitivities

| ELISA | Antigen type | Cutoff OD | Sensitivity (%) | Specificity (%) |
|---|---|---|---|---|
| Aspergillus | Oxidized | 0.85 | 89 | 95 |
| IgG | Nonoxidized | 0.23 | 89 | 65 |
| Blastomyces | Oxidized | 0.40 | 100 | 100 |
| IgG | Nonoxidized | 0.50 | 100 | 87 |

For comparative purposes, we determined the specificity of the *Histoplasma* IgG assay using nonoxidized antigen under conditions where the sensitivity using nonoxidized antigen matched that seen using oxidized antigen (i.e., 100%). Thus, the cutoff OD giving 100% sensitivity when using nonoxidized antigen was 0.50 (FIG. 1). Based on this cutoff OD value, the specificity of the *Histoplasma* IgG assay using nonoxidized antigen was only 25% (see Table 2). Thus, under conditions providing 100% sensitivity, oxidation of *Histoplasma* antigen profoundly improved the specificity of an ELISA for detecting *Histoplasma* IgG.

EXAMPLE 2

Detection of IgG Antibodies Recognizing *Coccidioides immitis*

*Coccidioides immitis* antigen (culture filtrate containing F antigen) intended for use in ID assays was purchased from a commercial source. Microtiter well preparation and assay performance was the same as described in Example 1 for *Histoplasma*, with the exception that conjugate was used at a final dilution of 1:5000 rather than 1:10000. The serum panel evaluated for *Coccidioides* IgG consisted of 80 samples previously tested for *Coccidioides* antibodies by ID (41 positive, 39 negative).

FIG. 2 presents the optical density (OD) values obtained following incubation of ID-positive and ID-negative serum samples in microtiter wells coated with nonoxidized and oxidized *Coccidioides* antigen. When using nonoxidized *Coccidioides* antigen as substrate, the distribution of OD values for the ID-negative serum group was similar to that observed for the ID-positive serum group. In contrast, when using the oxidized *Coccidioides* antigen as substrate, the distribution of values for the ID-negative serum group was markedly different from the distribution of values for the ID-positive serum group. When using the oxidized antigen, 37 of 41 (90%) ID-positive serum samples exhibited OD values >1.00, whereas only 1 of 39 (3%) ID-negative serum samples exhibited OD values >1.00. Expressed another way, the *Coccidioides* IgG assay using oxidized *Coccidioides* antigen as substrate was 90% sensitive and 97% specific (see Table 2) using an OD cutoff value of 1.00.

For comparative purposes, we determined the specificity of the *Coccidioides* IgG assay using nonoxidized antigen under conditions where the sensitivity using nonoxidized antigen matched that seen using oxidized antigen (i.e., 90%). Thus, the cutoff OD giving 90% sensitivity when using nonoxidized antigen was 0.22 (FIG. 2). Based on this cutoff OD value, the specificity of the *Coccidioides* IgG assay using nonoxidized antigen was only 28% (see Table 2). Thus, under conditions providing 90% sensitivity, oxidation of *Coccidioides* antigen profoundly improved the specificity of an ELISA for detecting *Coccidioides* IgG.

EXAMPLE 3

Detection of IgG Antibodies Recognizing *Aspergillus fumigatus*

*Aspergillus fumigatus* antigen (culture filtrate) intended for use in ID assays was purchased from a commercial source. Microtiter well preparation and assay performance was the same as described in Example 1 for *Histoplasma*, with the exception that conjugate was used at a final dilution of 1:5000 rather than 1:10000. The serum panel evaluated for *Aspergillus* IgG consisted of 29 samples previously tested for *Aspergillus* antibodies by ID (9 positive, 20 negative).

FIG. 3 presents the optical density (OD) values obtained following incubation of ID-positive and ID-negative serum samples in microtiter wells coated with nonoxidized and oxidized *Aspergillus* antigen. For both nonoxidized and oxidized antigen, the overall distribution of OD values for the ID-negative group was visually distinct from the distribution of OD values for the ID-positive group. However, the range of difference between the ID-negative distribution and the ID-positive distribution was more marked when using oxidized *Aspergillus* antigen. When using the oxidized antigen, 8 of 9 (89%) ID-positive serum samples exhibited OD values >0.85, whereas only 1 of 20 (5%) ID-negative serum samples exhibited OD values >0.85. Expressed another way, the *Aspergillus* IgG assay using oxidized *Aspergillus* antigen as substrate was 89% sensitive and 95% specific (see Table 2) using an OD cutoff value of 0.85.

For comparative purposes, we determined the specificity of the *Aspergillus* IgG assay using nonoxidized antigen under conditions where the sensitivity using nonoxidized antigen matched that seen using oxidized antigen (i.e., 89%). Thus, the cutoff OD giving 89% sensitivity when using nonoxidized antigen was 0.23 (FIG. 3). Based on this cutoff OD value, the specificity of the *Aspergillus* IgG assay using nonoxidized antigen was 65% (see Table 2). Thus, under conditions providing 89% sensitivity, oxidation of *Aspergillus* antigen markedly improved the specificity of an ELISA for detecting *Aspergillus* IgG.

EXAMPLE 4

Detection of IgG Antibodies Recognizing *Blastomyces dermatitidis*

*Blastomyces dermatitidis* antigen (culture filtrate containing A antigen) intended for use in ID assays was purchased from a commercial source. Microtiter well preparation and assay performance was exactly the same as described in Example 1 for *Histoplasma*. The serum panel evaluated for *Blastomyces* IgG consisted of 16 samples previously tested for *Blastomyces* antibodies by ID (1 positive, 15 negative).

FIG. 4 presents the optical density (OD) values obtained following incubation of ID-positive and ID-negative serum samples in microtiter wells coated with nonoxidized and oxidized *Blastomyces* antigen. When using the oxidized antigen, the single ID-positive serum sample exhibited an OD value >0.4, whereas only 0 of 15 (0%) ID-negative serum samples exhibited OD values >0.40. Expressed another way, the *Blastomyces* IgG assay using oxidized *Blastomyces* antigen as substrate was 100% sensitive and 100% specific (see Table 2) using an OD cutoff value of 0.40.

For comparative purposes, we determined the specificity of the *Blastomyces* IgG assay using nonoxidized antigen under conditions where the sensitivity using nonoxidized antigen matched that seen using oxidized antigen (i.e., 100%). Thus, the cutoff OD giving 100% sensitivity when using nonoxidized antigen was 0.50 (FIG. 4). Based on this cutoff OD value, the specificity of the *Blastomyces* IgG assay using nonoxidized antigen was 87% (see Table 2). Thus, under conditions providing 100% sensitivity, oxidation of *Blastomyces* antigen improved the specificity of an ELISA for detecting *Blastomyces* IgG.

EXAMPLE 5

Detection of IgG Antibodies Recognizing *Histoplasma capsulatum* Using Simultaneous Oxidation and Coating of Antigen

*Histoplasma capsulatum* antigen (culture filtrate containing both H and M antigens) intended for use in ID assays was purchased from a commercial source, and adjusted to 20 ug/mL in sodium acetate buffer containing 0.05 M periodate (hereafter referred to as oxidized antigen). The antigen solution was coated into microtiter wells together with sodium metaperiodate. For comparative purposes, a duplicate antigen suspension in sodium acetate buffer without periodate was prepared (hereafter referred to as nonoxidized antigen). Thus, some microtiter wells received *Histoplasma* antigen with periodate, whereas other wells received *Histoplasma* antigen without periodate. After an overnight incubation in the refrigerator, the *Histoplasma* antigen preparations (oxidized or nonoxidized) were discarded from the wells, and PBS containing 0.1% (w/v) BSA and 5% (w/v) trehalose was added to the wells as blocking agent. After 2 hours at room temperature, the blocking agent was discarded, and the plates were then air-dried at room temperature for 2 hours. After pouching, the plates were stored in the refrigerator.

On the day of assay, *Histoplasma*-coated microtiter wells (some with oxidized antigen, others with nonoxidized antigen) were allowed to come to room temperature. During this step, 80 serum samples previously tested for *Histoplasma* antibodies by ID (16 positive, 64 negative) were diluted 1:400 in sample dilution buffer (PBST containing BSA). Once the wells had reached room temperature (approximately 1 hour), they were washed once with PBST, and the wash solution discarded. Diluted serum samples were then added to duplicate microtiter wells (one containing oxidized *Histoplasma* antigen, the other containing nonoxidized *Histoplasma* antigen). The microtiter wells were covered with adhesive tape and incubated at room temperature for 1.5 hours. Following 4 washes with PBST, each well then received 0.1 mL of horseradish peroxidase-conjugated goat anti-human IgG (diluted 1:10000 in PBST), and incubation was continued for 1 hour at room temperature. Following another series of 4 washes, each well then received 0.1 mL of tetra-methylbenzidine; after 10 minutes at room temperature, the reaction was stopped by the addition of 0.1N hydrochloric acid. The optical density was measured at 450 nM using a spectrophotometric ELISA reader.

TABLE 3

Specificities of fungal IgG ELISAs using antigen oxidized during and prior to coating of wells giving the same sensitivities

| ELISA | Antigen Processing | Cutoff OD | Sensitivity (%) | Specificity (%) |
|---|---|---|---|---|
| Histoplasma Ab | Nonoxidized | 0.216 | 100 | 31 |
| | Oxidized during coating | 0.343 | 100 | 100 |
| | Oxidized prior to coating | 0.452 | 94 | 100 |

For comparative purposes, *Histoplasma* antigen used for the ELISA was coated either nonoxidized, oxidized prior to coating, or oxidized simultaneous with the coating process. See Table 3 above. A "Cutoff" serum sample was established that allowed for the maximum sensitivity for the *Histoplasma* ELISA for the three different antigen processing formats. Two of the 3 formats had 100% sensitivity and in one format a single positive serum sample was not considered positive. Based on the Cutoff OD value the specificity of the *Histoplasma* ELISA was only 31% when the nonoxidized antigen was used. The specificity for the *Histoplasma* ELISA using the oxidized antigen was 100% regardless of when the antigen was oxidized. Thus, oxidizing the antigen either prior or during the coating process provided the same profound improvement of assay specificity compared to nonoxidized antigen.

The above examples are included for illustrative purposes only and are not intended to limit the scope of the invention. Many variations to those described above are possible. Since modifications and variations to the examples described above will be apparent to those of skill in this art, it is intended that this invention be limited only by the scope of the appended claims.

What is claimed is:

1. A method of testing a sample to determine the presence and/or amount of an antibody to a fungal antigen, the method comprising:
    a) contacting the fungal antigen with an oxidizing agent in a suitable device to produce an oxidized fungal antigen attached to the surface of the device, wherein said oxidized fungal antigen attached to said device is suitable for testing an antibody to the fungal antigen;
    b) contacting a sample suspected of containing an antibody to a fungus with the device containing the attached oxidized fungal antigen produced in step b) under suitable conditions to allow binding of the antibody, if present in the sample, to the oxidized fungal antigen; and
    c) assessing binding between the antibody and the oxidized fungal antigen to determine the presence and/or amount of the antibody in the sample.

2. The method of claim 1, wherein said fungal antigen is a pathogenic fungus.

3. The method of claim 1, wherein the sample is a clinical sample.

4. The method of claim 3, wherein the sample is a human clinical sample.

5. The method of claim 1, wherein the fungal antigen has not been purified from the culture filtrate.

6. The method of claim 1, wherein the oxidizing agent is periodate.

7. The method of claim 1, wherein the binding between the antibody and the oxidized fungal antigen is assessed by a sandwich or competitive assay format.

8. The method of claim 1, wherein the binding between the antibody and the oxidized fungal antigen is assessed by a format selected from the group consisting of an enzyme-linked immunosorbent assay (ELISA), immunoblotting, immunoprecipitation, radioimmunoassay (RIA), immunostaining, latex agglutination, indirect hemagglutination assay (IHA), complement fixation, indirect immnunofluorescent assay (FA), nephelometry, flow cytometry assay, chemiluminescence assay, lateral flow immunoassay, u-capture assay, inhibition assay and avidity assay.

9. The method of claim 1, wherein the binding between the antibody and the oxidized fungal antigen is assessed by an ELISA format.

\* \* \* \* \*